(12) United States Patent
Lemer

(10) Patent No.: US 11,826,184 B2
(45) Date of Patent: Nov. 28, 2023

(54) EQUIPMENT FOR RECEIVING SURGICAL MATERIALS AND/OR LIQUID PRODUCTS

(71) Applicant: LEMER PAX, La Chapelle sur Erdre (FR)

(72) Inventor: Pierre-Marie Lemer, Nantes (FR)

(73) Assignee: LEMER PAX, La Chapelle sur Erdre (FR)

( * ) Notice: Subject to any disclaimer, the term of this patent is extended or adjusted under 35 U.S.C. 154(b) by 378 days.

(21) Appl. No.: 16/956,401

(22) PCT Filed: Dec. 14, 2018

(86) PCT No.: PCT/FR2018/053310
§ 371 (c)(1),
(2) Date: Jun. 19, 2020

(87) PCT Pub. No.: WO2019/122637
PCT Pub. Date: Jun. 27, 2019

(65) Prior Publication Data
US 2020/0330176 A1    Oct. 22, 2020

(30) Foreign Application Priority Data

Dec. 21, 2017   (FR) ...................................... 1762776

(51) Int. Cl.
*A61B 50/33*     (2016.01)
*A61B 50/13*     (2016.01)
(Continued)

(52) U.S. Cl.
CPC .............. *A61B 50/33* (2016.02); *A61B 50/13* (2016.02); *A61B 2050/0016* (2016.02);
(Continued)

(58) Field of Classification Search
CPC . A61B 50/33; A61B 50/13; A61B 2050/0066; A61B 2050/0016; A61B 2050/0086; A61B 2050/3006
(Continued)

(56) References Cited

U.S. PATENT DOCUMENTS 5,379,703 A * 1/1995 Marshall ................ A61B 50/13
108/90
5,871,015 A * 2/1999 Lofgren ................ A61B 50/13
128/849
(Continued)

FOREIGN PATENT DOCUMENTS

WO         9607364 A1    3/1996
WO      2014078553 A1    5/2014

OTHER PUBLICATIONS

International Search Report, dated Mar. 28, 2019, from corresponding PCT application No. PCT/FR2018/053310.

*Primary Examiner* — Steven A. Reynolds
(74) *Attorney, Agent, or Firm* — NIXON & VANDERHYE

(57) ABSTRACT

Disclosed is an equipment for receiving surgical materials and/or liquid products for a surgical procedure. The equipment includes: a tray with a top face; and a tight surface film intended to be removably attached to the top face of the tray in order to form a sterile upper surface that is intended to receive the surgical materials and/or liquid products. The top face of the tray includes at least one recess, and the tight surface film, attached to the tray, forms at least one pocket extending inside the at least one recess and adapted to receive at least one of the surgical materials and/or liquid products.

7 Claims, 4 Drawing Sheets

(51) Int. Cl.
    *A61B 50/00*    (2016.01)
    *A61B 50/30*    (2016.01)
(52) U.S. Cl.
    CPC ............... *A61B 2050/0065* (2016.02); *A61B 2050/0066* (2016.02); *A61B 2050/0086* (2016.02); *A61B 2050/3006* (2016.02); *A61B 2217/005* (2013.01)
(58) Field of Classification Search
    USPC ........................................................ 206/438
    See application file for complete search history.

(56) References Cited

U.S. PATENT DOCUMENTS

| | | | |
|---|---|---|---|
| 7,104,201 B2* | 9/2006 | Comeaux | A61B 46/10 |
| | | | 108/90 |
| 8,747,739 B2* | 6/2014 | Parker | A61B 50/00 |
| | | | 422/294 |
| 9,393,075 B2* | 7/2016 | Ghosh | A61B 46/10 |
| 2003/0056698 A1 | 3/2003 | Comeaux | |
| 2011/0192744 A1* | 8/2011 | Parker | A61B 50/30 |
| | | | 206/363 |
| 2014/0046451 A1* | 2/2014 | Liccardo | A61F 2/0095 |
| | | | 623/20.35 |
| 2015/0096475 A1* | 4/2015 | Lee | A47B 97/00 |
| | | | 108/50.11 |

* cited by examiner

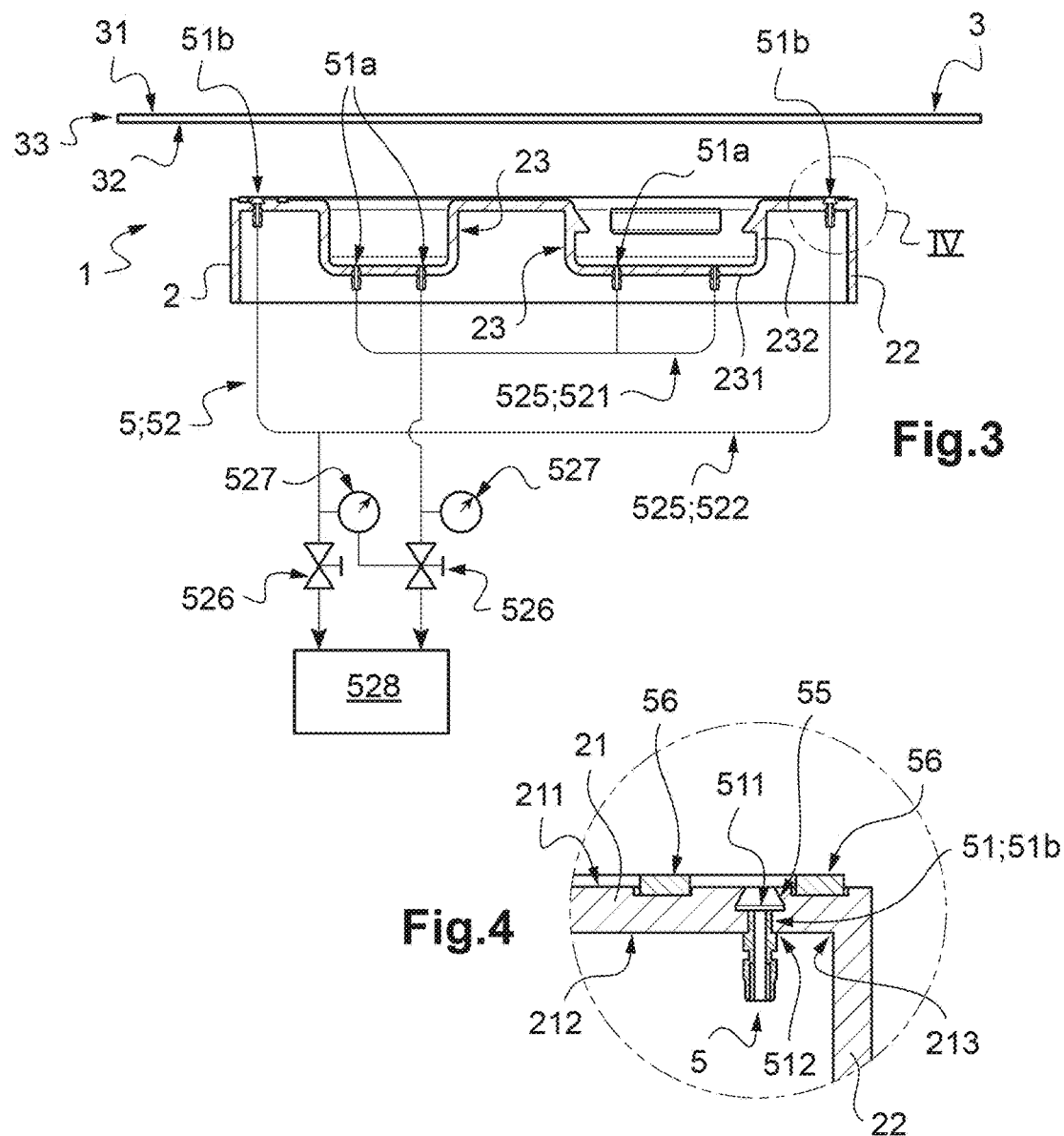
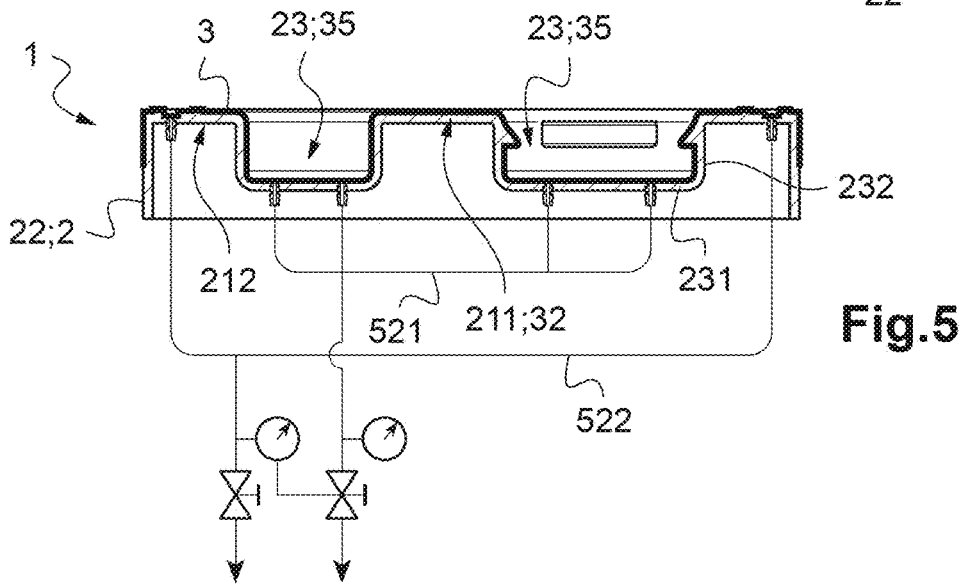

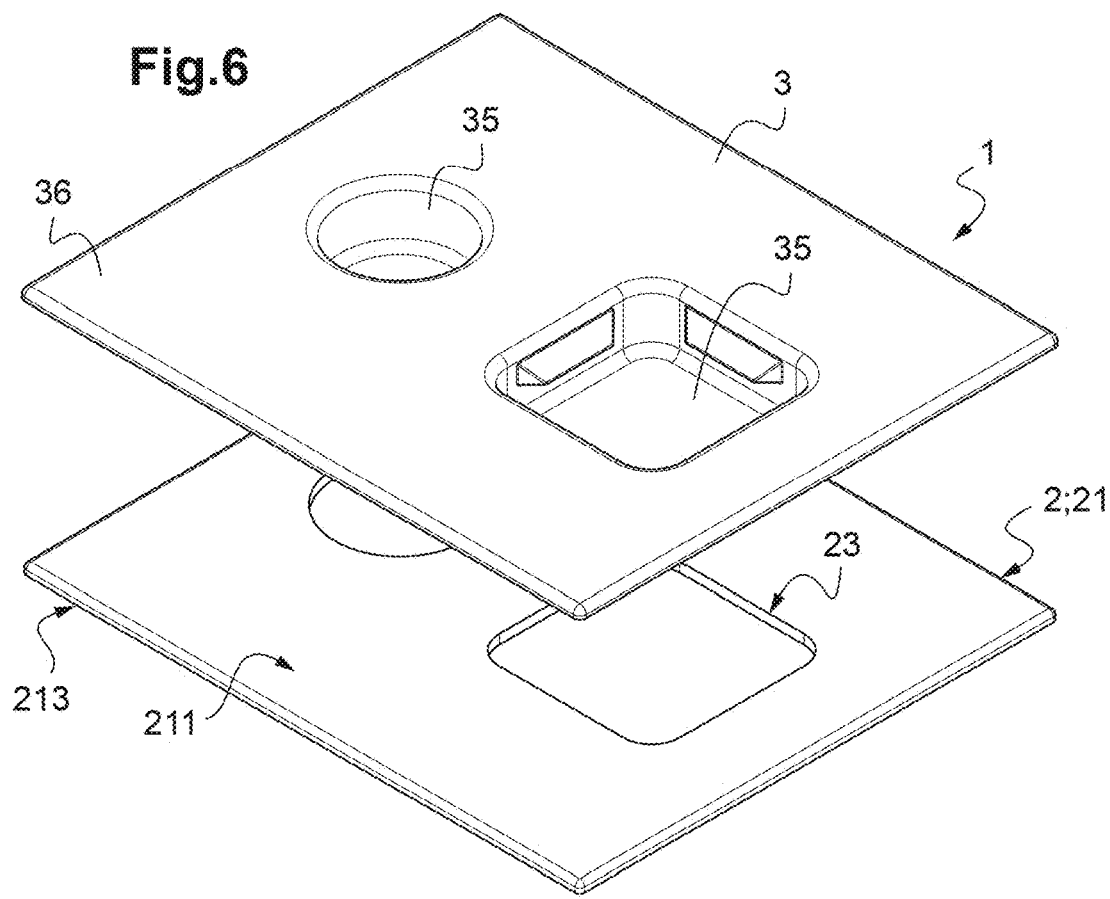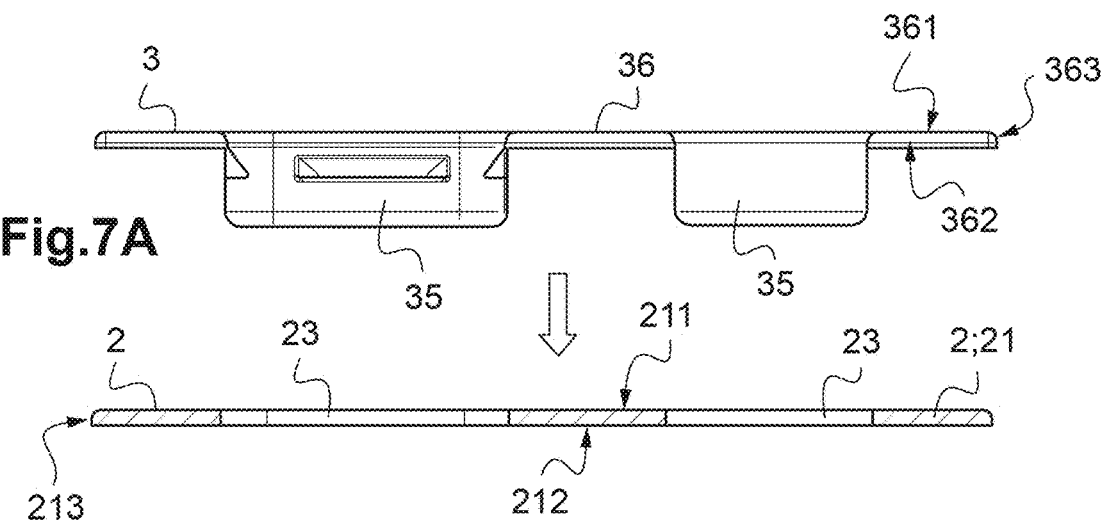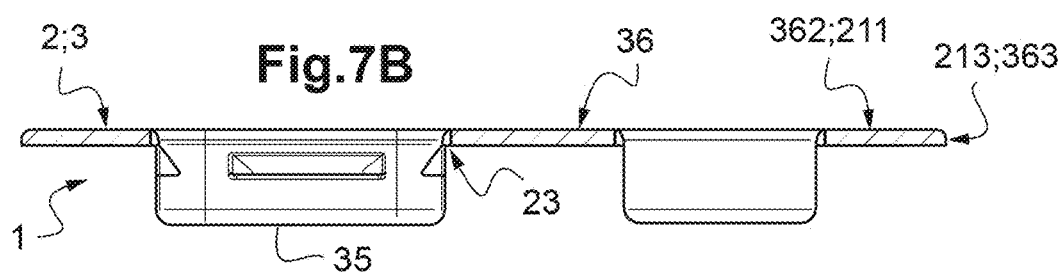

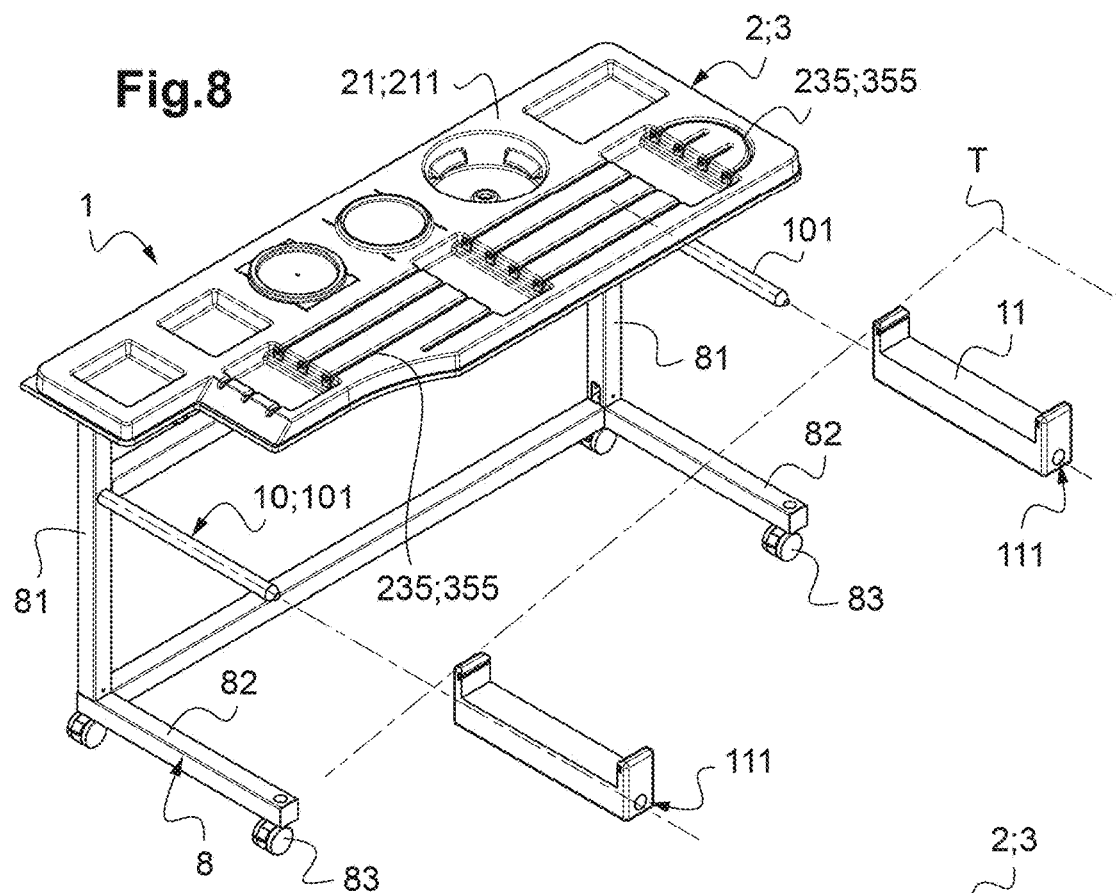
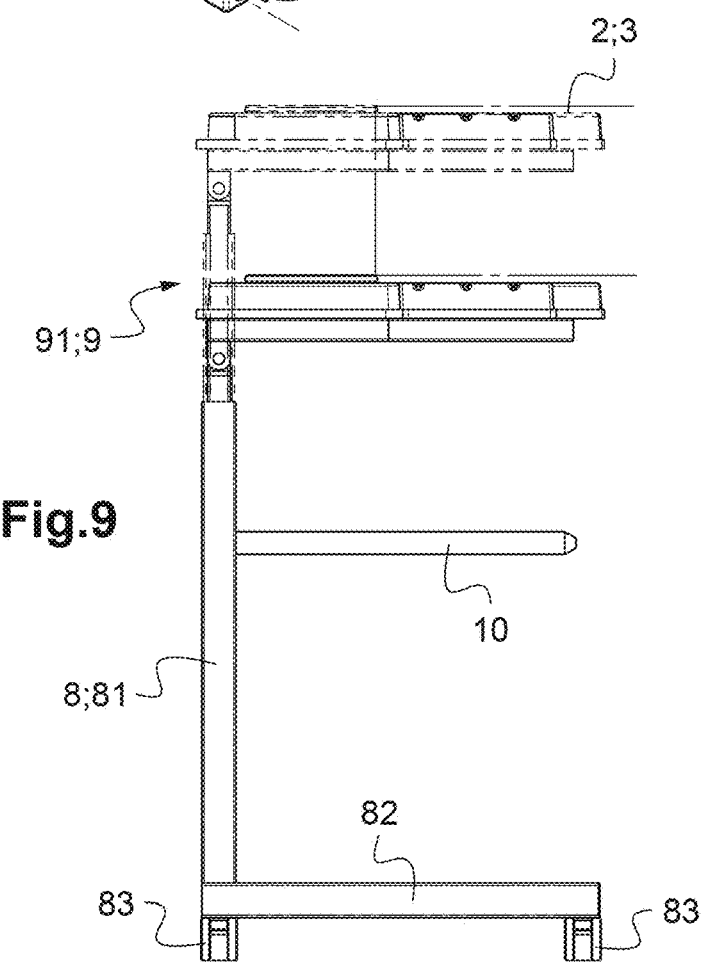

EQUIPMENT FOR RECEIVING SURGICAL MATERIALS AND/OR LIQUID PRODUCTS

TECHNICAL FIELD TO WHICH THE INVENTION RELATES

The present invention generally relates to the field of operating room equipment.

It more particularly relates to an equipment for receiving surgical materials and/or liquid products, which are intended to be used by a practitioner during a surgical procedure.

TECHNOLOGICAL BACK-GROUND

An operating room contains all the appliances and materials required for practicing a surgical procedure.

This operating room contains in particular items of equipment such as trolleys for supporting the different materials required for the procedure, i.e. for example different receptacles or containers, pads, catheters, syringes, surgical instruments (such as clamps, chisels, etc.).

Such a trolley comprises a tray that has a planar upper surface, usually covered with a sterile and tight non-woven film, on which the different surgical materials are intended to be distributed.

But the current trolley structures are not fully satisfying.

Firstly, the application of the non-woven film onto the tray is not always easy.

Also, the planar aspect of the upper surface of the tray does not allow an optimum positioning and holding of the materials.

Moreover, the receptacles or containers, used for receiving certain liquids and instruments, are often single-use and constitute a high volume of wastes that then generates problems of storage and elimination.

Items of equipment such as trolleys are conventionally positioned behind the practitioner, who thus must turn around, on several occasions, to have access to the required materials.

There hence exists a need for a new equipment for operating room, whose tray has an upper surface that would be adapted for an optimum positioning of the tight surface film, a better ergonomics in receiving surgical instruments, and also a reduction of the volume of wastes generated.

OBJECT OF THE INVENTION

In order to remedy the above-mentioned drawback of the state of the art, the present invention proposes an equipment for receiving surgical materials and/or liquid products, wherein said equipment comprises:
- a tray having an upper face, and
- a tight (or leak-tight or fluid-tight or liquid/air-tight) surface film, intended to be removably applied onto said upper face of said tray to form a sterile upper surface intended to receive said surgical materials and/or said liquid products.

According to the invention, said upper face of said tray includes at least one housing; and said tight surface film, applied onto said tray, forms at least one recess that extends into said at least one housing and that is adapted to receive one at least of said surgical materials and/or liquid products.

The tray is hence adapted for an optimum positioning of the sterile tight surface film.

Moreover, the tight surface film is intended to form a sterile upper surface that provides a better ergonomics in receiving surgical instruments. And the recess, consisted of the film portion that is associated with the tray housing, may allow replacing a receptacle or container of the state of the art.

According to a first particular embodiment, the tight surface film consists of a flexible film intended to conform the upper face of the tray, and the tray includes means for sticking said tight surface film against its upper face.

The sticking means advantageously comprise channels formed in said tray. One at least of said channels comprises:
- an upstream end, opening to the upper face of said tray, and
- a downstream end, intended to be connected with air suction means, so as to cause a suction sticking of said tight surface film against said upper face of said tray.

Other non-limitative and advantageous features of this first embodiment, taken individually or according to all the technically possible combinations, are the following:
- said at least one channel is arranged so that its upstream end opens to said at least one housing of the upper face of the tray;
- the tray includes a peripheral band surrounding said at least one housing and to which opens one at least of said channels; the peripheral band advantageously consists of a groove to which opens said at least one channel; the peripheral band is advantageously lined with at least one sealing gasket, advantageously two sealing gaskets arranged on either side of said groove;
- several channels open to said peripheral band, whose respective upstream ends are distributed over the length of said peripheral band;
- the equipment includes piloting means for adjusting the suction flow rate generated by the air suction means, wherein said piloting means has two operating configurations: an initial operating configuration, for piloting the suction flow rate to a first value, and a holding operating configuration, for piloting the suction flow rate to a second value, lower than said first value.

Still according to the first particular embodiment:
- the sticking means advantageously comprise heating means, adapted to cause a deformation of said tight surface film so that the latter conforms said upper face of the tray; for example, the tight surface film consists of a resistive or thermoformable film allowing heating said film with an electric current;
- the tight surface film advantageously comprises an edge that is provided with an elastic member and that is intended to be advantageously received in an annular groove,
- the tight surface film comprises a main wall, comprising a part formed by a flexible sheet made of an unwoven or non-woven material, and recesses, comprising parts in the form of pockets, made of a plastic material.

According to a second particular embodiment, the tight surface film consists of a semi-rigid film or a rigid film, wherein said at least one recess is preformed.

Generally, the equipment advantageously comprises an underframe carrying the tray, wherein said underframe comprises:
- means for adjusting said tray in height, and/or
- means for detachably fastening said underframe with complementary receiving means equipping an operation table intended to receive a patient.

The invention also proposes a tight surface film, intended to be removably applied onto a tray belonging to an equipment according to the invention, to form a sterile upper surface forming at least one recess that is adapted to receive one at least of said surgical materials and/or liquid products.

The invention also relates to a tray for an equipment for receiving surgical materials and/or liquid products, wherein said tray has an upper face that is provided with at least one housing and that is intended to removably receive the tight surface film intended to form at least one recess for receiving said surgical materials and/or liquid products.

DETAILED DESCRIPTION OF AN EXEMPLARY EMBODIMENT

The following description in relation with the appended drawings, given by way of non-limitative example, will allow a good understanding of what the invention consists of and of how it can be implemented.

In the appended drawings:

FIG. 3 is a sectional view of the tray of FIG. 2, according to a sectional plane III-III shown in FIG. 2, with a flexible tight surface film before the fitting thereof;

FIG. 4 is an enlarged view of the detail IV of FIG. 3, showing the structure of the peripheral band surrounding the housings of the tray;

FIG. 5 shows the tray of FIG. 3, whose upper face is covered with the flexible tight surface film, to form a sterile upper surface provided with recesses adapted to receive the surgical materials;

Figure 1:
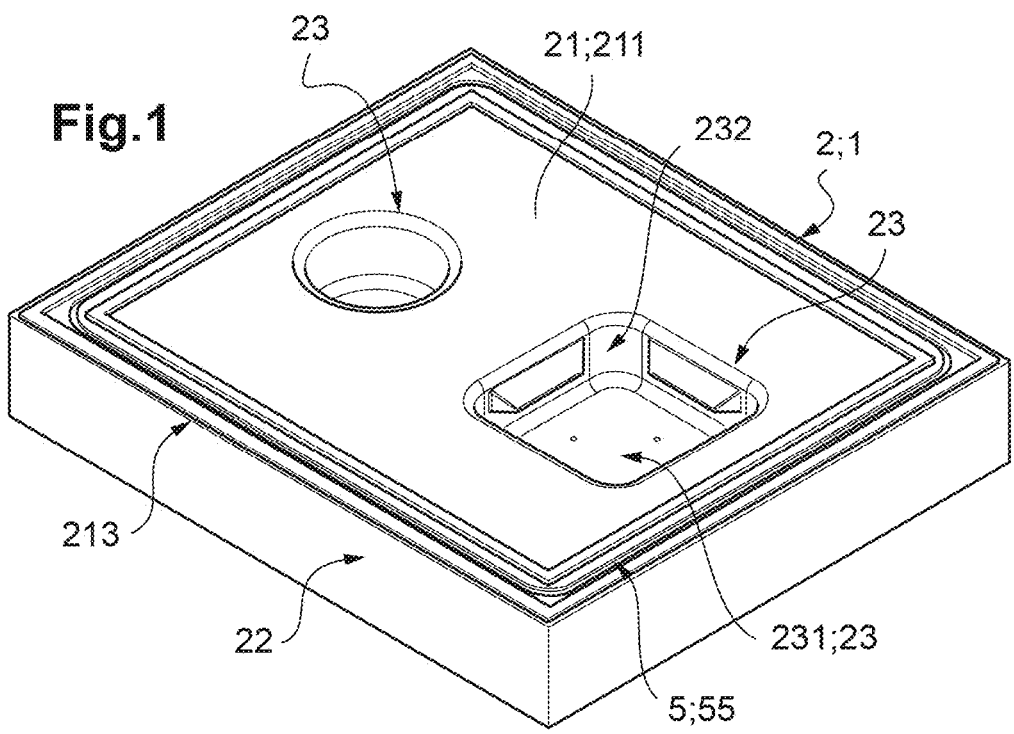
FIG. 1 is a schematic overall and perspective view of a tray intended to equip an equipment according to a first embodiment.

FIG. 6 schematically shows a second embodiment of the equipment according to the invention, wherein the tray is intended to be associated with a rigid/semi-rigid tight surface film;

FIG. 7 is a sectional view of FIG. 6, which shows, on the one hand, the tight surface film located above and remote from the tray (FIG. 7A) and, on the other hand, the same tight surface film suitably mounted on the tray (FIG. 7B);

FIG. 8 shows a variant embodiment of the equipment according to the invention, wherein the tray/tight surface film unit is carried by an underframe;

FIG. 9 is a side view of the equipment according to FIG. 8, to show in particular the means for adjusting the tray in height.

The equipment 1 according to the invention is intended to equip an operating room.

By "operating room", it is meant a part of an operating theatre serving to practice a surgical procedure on a patient.

Such an operating room conventionally contains, on the one hand, an operating table T (whose edge is very schematically and partially shown in FIG. 8, in dashed lines), intended to receive a patient, and on the other hand, all the materials required for each type of procedure.

The equipment 1 according to the invention is advantageously in the general form of a trolley that is intended to serve as a support surface for putting and distributing the surgical materials (such as containers, clamps, chisels, catheters, pads, etc.) and/or liquid products.

Generally, the equipment 1 comprises two main elements:
a tray 2, serving as a support structure, and
a tight surface film 3 (shown in FIGS. 3, 6 and 7), intended to be removably applied onto said tray 2 to form a sterile upper surface intended to receive the surgical materials and/or the liquid products.

The tray 2 advantageously consists of a part of generally parallelepipedal shape, or also in the general shape of a panel or a plate.

This tray 2 comprises a main wall 21 that has two opposite faces: an upper face 211, forming the upper face of the tray 2, and a lower face 212.

This main wall 21 also comprises a peripheral edge 213, corresponding to the edge/periphery of the tray 2.

According to the invention, the tray 2 and the tight surface film 3 are complementary of each other to receive the surgical materials and/or the liquid products:
the upper face 211 of the tray 2 comprises housings 23, and
the tight surface film 3, applied onto this tray 2, forms recesses 35 that extend within these housings 23 and that are adapted to receive the surgical materials and/or the liquid products (FIGS. 5 and 7).

In a first embodiment shown in FIGS. 1 to 5, the tray 2 includes means 5 for sticking the tight surface film 3 against the upper face 221 of the tray 2. The tight surface film 3 hence consists of a flexible film intended to conform the upper face 211 of the tray 2.

Herein, the tray 2 advantageously consists of a single-piece part, made for example of a plastic material, preferably acrylonitrile butadiene styrene.

The peripheral edge 213 of the main wall 21 of the tray 2 is here extended by a skirt 22 that extends on the side of the lower face 212 of this main wall 21.

The housings 23 the tray 2 consist of blind-holes (or concavities) that are made single-piece at the main wall 21 of the tray 2 and that open upward on the side of the upper face 211.

The housings 23 have hence a concave shape with respect to the upper face 211 of the main wall 21. In other words, these housings 23 protrude on the side of lower face 212 of the main wall 21.

Each housing 23 here comprises a bottom wall 231 and a lateral wall 232.

Figure 2:
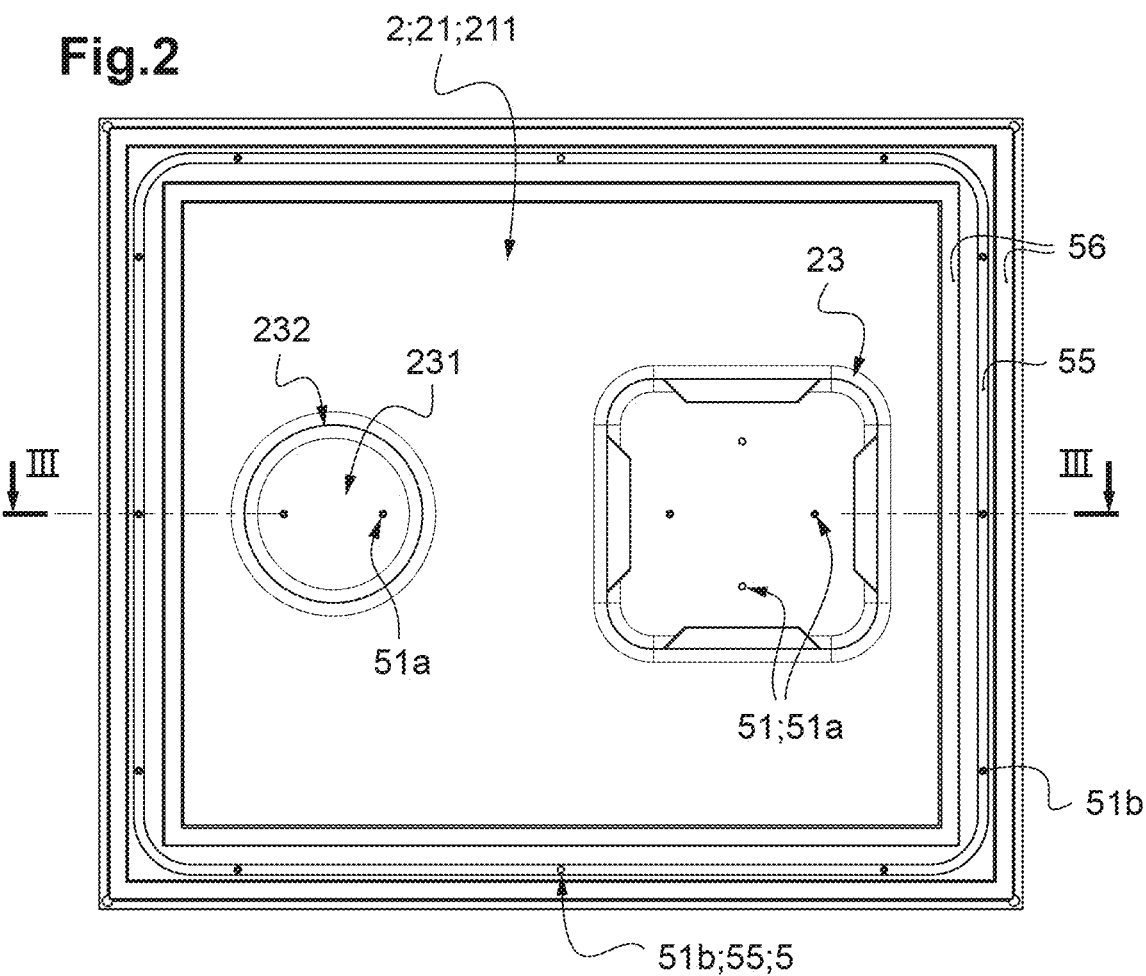
FIG. 2 is a top view of the tray according to FIG. 1.

Each housing 23 can have various shapes, for example cylindrical or parallelepipedal, as illustrated by way of example in FIGS. 1 and 2.

The housings 23 have for example a depth from 50 to 150 mm, with sides from 50 to 400 mm.

The sticking means 5 here consist of means for sticking the tight surface film 3 by an air suction phenomenon.

For that purpose, the sticking means 5 comprise a set of channels 51 that are formed in the tray 2 and that are intended to be connected to air suction means 52.

As illustrated in FIG. 4, each channel 51 extends in the thickness of the main wall 21 of the tray 2.

Each channel 51 has two ends:
an upstream end 511, opening to the upper face 211 of the tray 2, and
a downstream end 512, opening to the lower face 212 of the main wall 21 and intended to be connected to the air suction means 52.

Each channel 51 has advantageously a constant diameter over its length, for example from 5 to 20 mm.

These channels 51 are here classified into two groups:
first, central, channels 51a are arranged so that their upstream end 511 opens to one of the housings 23 of the tray 2, and
second, peripheral, channels 51b are arranged so that their upstream end 511 opens to a peripheral band 55 surrounding the housings 23.

The first channels 51a are intended to ensure a suction sticking of the tight surface film 3 inside the housings 23, so as to form the above-mentioned recesses 35.

The second channels 51b are provided to ensure a peripheral tightness between the main wall 21 and the tight surface film 3.

As shown in FIG. 4, to optimize this tightness, the peripheral band 55 consists of a groove formed in the upper surface 211 of the tray 2, along the peripheral edge 213 of the main wall 21.

This groove 55 has herein a cross-section of generally trapezoidal shape with, on the one hand, its lower, great side to which open the second channels 51b, and on the other hand, its upper, small side opening to the upper surface 211 of the tray 2.

The particular cross-section has for interest to ensure a tightness and an optimum holding of the tight surface film 3 against the tray 2.

Several second channels 51b open to the peripheral band 55, whose upstream ends 511 are distributed over the length of the latter (suitably to obtain the searched tightness).

For example, this peripheral band 55 has the following dimensions:
  width of its great base from 10 to 30 mm,
  width of its small base from 5 to 20 mm, and
  depth from 5 to 15 mm.

This peripheral band 55 is here lined with sealing gaskets 56, advantageously two sealing gaskets 56 arranged on either side of the peripheral band 55 (i.e. inward of the peripheral band 55, for one of them, and outward of the peripheral band 55, for the other one).

Each sealing gasket 56 is in the form a band made for example of a plastic material, for example a silicone foam.

The peripheral band 55 forms a closed loop that surrounds the housing(s) 23; and the two sealing gaskets 56 each form a closed loop that follows the inner and outer peripheries of the peripheral band 55.

Each sealing gasket 56 protrudes with respect to the upper face 211 of the tray 2, so as to be compressed during the suction sticking of the tight surface film 3.

For example, this sealing gasket 56 has the following dimensions:
  a width from 10 to 20 mm,
  a protrusion height from 3 to 10 mm.

As shown in FIG. 3, the air suction means 52, connected to the channel 51, advantageously comprise two circuits:
  a first suction circuit 521, connected to the first channels 51a (opening to the housings 23), and
  a second suction circuit 522, connected to the second channels 51b (opening to the groove-shaped peripheral band 55, in the bottom of the latter).

Each of the two circuits 521, 522 advantageously comprises a set of tubes 525, equipped with a valve 526 and a vacuum switch 527.

The tubes 525 of each circuit 521, 522 are connected, on an upstream side, with a group of channels 51a or 51b, and, on a downstream side, with an air suction device 528.

As an alternative, not shown, the tubes 525 can be replaced by chambers or boxes that are formed single-piece, directly in the tray 2 (under the main wall 21).

The air suction device 528 consists, for example, of a pneumatic vacuum generator (venturi effect) or of an electric vacuum generator (vacuum pump).

The air suction means that are conventionally found in the operating rooms are advantageously used.

The valves 526 advantageously consist of solenoid valves that are adapted to adjust the suction flow rate generated at the associated channels 51a or 51b.

The vacuum switches 527 are vacuum detectors that allow detecting the vacuum generated within the channels 51. They output a signal (electronic or mechanical) indicating the vacuum value.

These vacuum switches 527 advantageously intervene as means for piloting the valves 526, to adjust the suction flow rate generated by the air suction means 5 within each of both suction circuits 521, 522.

Herein, the vacuum switch 527 equipping the second circuit 522 (connected to the second channels 51b) is connected to the valve 526 of the first circuit 521 (connected to the first channels 51a).

The vacuum switch 527 of the second channel 522 is hence intended to pilot the valve 526 of the first circuit 521, so as to trigger the opening thereof when a threshold vacuum value is reached.

Likewise, these vacuum switches 527 advantageously take two operating configurations:
  an initial operating configuration, for piloting the suction flow rate to a first, relatively high, value that ensures the optimum sticking of the tight surface film 3 against the upper face 211 of the tray 2 (including inside the housings 23), and
  a holding operating configuration, for piloting the suction flow rate to a second value, lower than said first value, that ensures the holding of tight surface film 3 in position against the upper face 211 of the tray 2.

For example, the vacuum values are the following:
  in the initial operating configuration: 200 mbar to 900 mbar, and
  in the holding operating configuration: 200 mbar to 900 mbar.

The tight surface film 3, intended to be applied onto such a tray 2, is advantageously made of a polymer material, i.e. polyamide/polyester, polyamide/ethylene vinyl alcohol (EVOH) copolymer/polyethylene.

This tight surface film 3 has advantageously a thickness comprised between 75 and 150 µm.

Moreover, it is advantageously:
  disinfectant-resistant,
  provided with shape memory,
  provided with high elongation, and
  devoid of elasticity.

This tight surface film 3 must also be vacuum tight and tight to hospital waste products.

The lower face of the tight surface film 3 can be covered, at least partially, with a layer of an electrically conductive material (allowing heating said film with an electric current for its thermoforming).

As shown in FIG. 3, this tight surface film 3 comprises in particular two opposite surfaces: an upper surface 31 and a lower surface 32.

This tight surface film 3 is also delimited by a peripheral edge 33 whose shape corresponds, at least approximately, to the edge 213 of the main wall 21 of the tray 2.

The tight surface film 3 can be supplied as a roll, or cut to the size of the tray 2 (potentially preformed), advantageously packed in a sterile individual bag.

The edge 33 of this tight surface film 3 can be equipped with an elastic member so as to optimize its holding on the tray 2.

In this case, the tray 2 can potentially comprise an annular groove within which this "elastic" edge 33 of the tight surface film 3 is intended to be received.

In a variant embodiment, the edge 33 of the flexible film 3 can comprise adhesive tapes suitable for maintaining its positioning on the tray 2 before the implementation of the suction means 5.

The fitting of the tight surface film 3 onto the tray 2 will be described hereinafter in relation with FIG. 5.

To perform this fitting, an operator first applies the tight surface film 3 onto the tray 2 so that its lower surface 32 bears on the upper face 211 of the main wall 21.

During this positioning, the operator makes sure that the tight surface film 3 covers the peripheral band 55 so as to be able to generate a continuous peripheral tightness.

The air suction means 52 are operated before, simultaneously with or after this application of the tight surface film 3 onto the tray 2.

In particular, the air suction device 528 is operated, and the valve 526 of the second suction circuit 522 is open.

A vacuum phenomenon is thus generated within the peripheral band 55, by the second suction circuit 522.

When a vacuum threshold value is reached, the vacuum switch 527 of this second peripheral circuit 522 causes the piloting and the opening of the valve 526 equipping the first circuit 521.

This opening thus allows generating the air suction and vacuum phenomenon within the housings 23 of the tray 2, so that the tight surface film 3 also comes and sticks within these housings 23 by a so-called "vacuum stamping" phenomenon.

The tight surface film 3 is also locally deformed so as to conform the bottom 231 and lateral 232 walls of each housing 23 (FIG. 5).

This tight surface film 3 forms directly the recesses 35 within each of the housings 23.

Preferably, the tight surface film 3 is adapted to stay in the shape of the upper surface 211 of the tray 2 (including the housings 23) should the vacuum being degraded.

Then, the vacuum switches 527 pilot the valves 526 so that the suction flow rate generated by the air suction means 52 ensures the holding of the tight surface film 3 on the tray 2.

A sterile tray 2/tight surface film 3 couple, as schematically shown in FIG. 5, is hence obtained.

The tight surface film 3, applied onto the tray 2 and conforming the upper surface 211 thereof, hence forms a sterile upper surface provided with recesses 35 that each extend within one of the housings 23 of the tray 2 and that are each adapted to receive one at least of the surgical materials (not shown) and/or liquid products.

Once the operation finished, the suction means can be used to suck up the liquids liable to cover the tight surface film 3 (in particular the liquids potentially present in the recesses 35).

Likewise, the operator just has to stop the sticking means 5, then to dissociate the tight surface film 3 from the tray 2 in order to fit a new tight surface film 3.

In a variant embodiment not shown, complementary or alternative of that described in relation with FIGS. 1 to 5, the equipment 1 can be equipped with sticking means comprising heating means that are adapted to cause (or to participate to) the deformation of the tight surface film 3 so that the latter conforms the upper face 211 of the tray 2.

These heating means would in particular be adapted to ensure a rising in temperature of the upper face 211 of the tray 2, for example to at least 80° C.

In this case, the tight surface film 3 would advantageously have thermoforming properties.

The lower face of the tight surface film 3 can be covered, at least partially, with a layer of an electrically conductive material (allowing heating said film with an electric current for its thermoforming). The equipment 1 also advantageously comprises means for powering said electrically conductive material layer.

After use, the tight surface film 3 can be folded over itself and discarded with potentially other single-use materials used during the procedure. Potentially, the flexible film 3 can be inserted at this moment into a seal bag provided with vacuuming means, in order to reduce the volume thereof.

In a second embodiment shown in FIGS. 6 and 7, the equipment 1 comprises a tight surface film 3 that consists of a semi-rigid film or a preformed rigid film.

This equipment 1 is hence relatively similar to that described hereinabove in relation with FIGS. 1 to 5 in that it comprises a tray 2 intended to removably receive the tight surface film 3.

Herein, the housings 23 are in the form of through-orifices, opening to the upper 211 and lower 212 faces of the main wall 21. As a variant, the orifices 23 can be replaced by blind housings.

The through-orifices 23 advantageously have a perimeter, corresponding to within the clearance, to that of the recesses 35 formed in the applied tight surface film 3.

For its part, the tight surface film 3, intended to be applied onto such a tray 2, is advantageously made of a plastic material, i.e. for example polyethylene terephthalate, polyamide/polyethylene, polyamide/ethylene vinyl alcohol copolymer/polyethylene.

This tight surface film 3 has for example a thickness comprised between 75 and 150 µm.

The recesses 35 are here preformed in the tight surface film 3, by any suitable technique.

This tight surface film 3 hence comprises a main wall 36 in which are preformed the recesses 35.

For example, the main wall 36 is in the form of a planar portion having an upper surface 361 and a lower surface 362.

The recesses 35 consist of concavities that are made single-piece in the main wall 36 and that open upward to the upper surface 361.

The recesses 35 hence have a concave shape with respect to the upper surface 361 of the main wall 36. In other words, these recesses 35 protrude on the side of the lower surface 362 of the main wall 36.

Each recess 35 can have various shapes, for example cylindrical or parallelepipedal, as illustrated by way of example in FIGS. 6 and 7.

This main wall 36 is also provided with an edge 363 in the form of a peripheral lip directed towards the above-mentioned lower face 362. This edge 363 corresponds, to within the clearance, to the edge 213 of the main wall 21 of the tray 2.

The implementation of this second embodiment is illustrated by FIG. 7.

For that purpose, the tight surface film 3 is positioned above the tray 2, with its preformed recesses 35 directed towards the tray 2 (FIG. 7A).

The tight surface film 3 is then handled by the operator so that:

the preformed recesses 35 each come and insert through one of the complementary housings 23 of the tray 2, and the lower face 362 of the main wall 36 of the tight surface film 3 comes and covers the upper face 211 of the main wall 21 of the tray 2.

A tray 2/tight surface film 3 couple, as schematically shown in FIG. 7B, is hence obtained.

The recesses 35 are each adapted to receive one at least of the surgical materials (not shown) and/or the liquid products.

Once the operation finished, an operator just has to dissociate the tight surface film 3 from the tray 2 in order to fit a new tight surface film 3.

The tight surface film 3 can comprise one or several folding lines to limit the bulk thereof before and/or after the use thereof.

The corresponding equipment 1 also advantageously comprises means that allow the detachable fastening between the film 3 and the tray 2. These fastening means can consist in adhesive tapes judiciously distributed over the peripheral edge 33 of the film 3; suction means, identical or similar to those described hereinabove in relation with FIGS. 1 to 5, can also be provided in the tray 2.

According to still an embodiment, not-shown, the tight surface film 3 is made by association of parts made of two different materials (described hereinafter in relation with FIG. 6 for the sake of understanding):
- a main wall 36, for example a part formed by a flexible sheet made of an unwoven or non-woven material, and
- recesses 35, for example parts in the form of flexible or rigid pockets, made of a plastic material.

The recesses 35 are added on the main wall 36, for example by sewing or welding. In particular, an upper edge of the recesses 35 is advantageously fastened with an edge of an orifice formed in the main wall 36.

FIGS. 8 and 9 represent a variant of two embodiments described hereinabove in relation with FIGS. 1 to 7.

Such an equipment 1 comprises the tray 2/tight surface film 3 unit according to the invention (as described hereinabove in relation with FIGS. 1 to 7), here associated with a rolling underframe 8.

The structure of the tray 2/tight surface film 3 unit is not limitative.

In particular, certain housings 235/recesses 355 couples have generally the shape of groove(s), adapted for receiving catheters.

This underframe 8 is made by the assembly of metallic profiles, in particular vertical posts 81 associated with longitudinal stringers 82 provided with casters 83.

The underframe 8, and in particular the posts 81, are equipped with means 9 for adjusting the tray 2 in height.

These adjustment means 9 consist for example of telescopic posts 91 that cooperate in translation with the posts 81 of the underframe 8 (schematically shown in FIG. 9).

These adjustment means 9 allow for example adjusting the height of the tray 2 over a height of 30 cm, with for example a maximum height of 1.5 m.

This technical feature can be useful in order to position the tray 2 above an operating table T, so as to allow the operators to have operating material available just above the patient.

The underframe 8 can also be equipped with detachable fastening means 10, for the detachable fastening of said underframe 8 with complementary receiving means 11 equipping the operating table T.

The detachable fastening means 10 of the equipment 1 consist for example of two arms 101, horizontal and parallel to each other, extending under the tray 2 from the posts 81.

The complementary receiving means 11 are in the form of sleeves 11 that equip the operating table T and that are intended to receive the arms 101 by fitting engagement.

Each sleeve 11 comprises in particular a cylindrical orifice 111, complementary of the arms 101 equipping the detachable fastening means 10.

Each sleeve 11 advantageously cooperates with its arm 101 through an indexing finger or a pressing screw.

In practice, the tight surface film 3 is conventionally applied onto the tray 2 of the equipment 1 (as developed hereinabove in relation with FIGS. 1 to 7).

The tray is then adjusted in height using the adjustment means 9.

The equipment 1 is then rolled so that its detachable fastening means 10 come into cooperation with the complementary receiving means 11 equipping the operating table T.

The equipment 1 carried by the operating table T can be moved upward/downward, but also frontally (front/rear) and/or laterally (left/right), by the operating means that equip the table T.

After the procedure, the used tight surface film 3 can be replaced by a new one on the tray 2, for a latter procedure.

The equipment 1 according to the invention allows optimizing the operations of fitting and removal of the tight film 3 on the associated tray 2; it can in particular allow limiting, of even suppressing, the use of certain voluminous materials or accessories of the container/receptacle type, usually necessary, and thus reducing the costs and volumes of the materials and wastes.

The invention claimed is:

1. An equipment for receiving surgical materials and/or liquid products for a surgical procedure, wherein said equipment (1) comprises:
   a tray (2) having a main wall (21) that has two opposite faces: an upper face (211) forming an upper face of the tray (2), and a lower face (212), said main wall (21) comprising a peripheral edge (213) corresponding to a periphery edge of the tray (2), and
   a tight surface film (3), intended to be removably applied onto said upper face (211) of said tray (2) to form a sterile upper surface intended to receive said surgical materials and/or liquid products,
   wherein said upper face (211) of said tray (2) comprises at least one housing (23),
   wherein said tight surface film (3), applied onto said tray (2), forms at least one recess (35) that extends into said at least one housing (23) and that is adapted to receive at least one of said surgical materials and/or liquid products,
   wherein the tight surface film (3) consists of a flexible film intended to conform the upper face (211) of the tray (2),
   wherein the tray (2) includes means (5) for sticking said tight surface film (3) against said upper face (211) of the tray (2),
   wherein the sticking means (5) comprise channels (51) formed in said tray (2),
   wherein at least one of said channels (51) comprises:
   an upstream end (511), opening to the upper face (211) of said tray (2), and
   a downstream end (512), intended to be connected with air suction means (52),
   so as to cause a suction sticking of said tight surface film (3) against said upper face (211) of said tray (2),
   wherein said at least one channel (51) is arranged so that the upstream end (511) of the at least one channel opens to said at least one housing (23) of the upper face (211) of the tray (2), wherein the tray (2) includes a peripheral band (55) surrounding said at least one housing (23) of the tray (2), the peripheral band opens to at least one of said channels (51), and wherein the peripheral band (55) consists of a groove which opens said at least one channel (51), said groove being formed in said upper surface (211) of the tray (2), along the peripheral edge (213) of the main wall (21).

2. The equipment according to claim 1, wherein the sticking means (5) comprise heating means, adapted to cause a deformation of said tight surface film (3) so said tight surface film conforms said upper face (211) of the tray (2).

3. The equipment according to claim 1, wherein the tight surface film (3) comprises:

a main wall (36), comprising a part formed by a flexible sheet made of an unwoven or non-woven material, and said at least one recess (35) comprises plural recesses (35), comprising parts in the form of pockets, made of a plastic material.

4. The equipment according to claim 1, further comprising an underframe (8) carrying the tray (2), wherein said underframe (8) comprises:

means (9) for adjusting said tray (2) in height, and/or means (10) for detachably fastening said underframe (8) with complementary receiving means (11) equipping an operation table (T) intended to receive a patient.

5. The tight surface film, intended to be removably applied onto a tray (2) belonging to an equipment (1) according to claim 1, to form said sterile upper surface forming said at least one recess (35) that is adapted to receive said at least one of said surgical materials and/or liquid products, wherein the tight surface film (3) consists of a flexible film intended to conform the upper face (211) of the tray (2), wherein said tight surface film comprises one of:

i) an edge that is provided with an elastic member and that is intended to be advantageously received in an annular groove of the tray, and ii) an edge of the tight surface film comprising adhesive tapes suitable for maintaining its positioning on the tray before the implementation of suction means.

6. The tray for an equipment (1) for receiving surgical materials and/or liquid products, according to claim 1, wherein said tray (2) has said upper face (211) that is provided with said at least one housing (23) and that is intended to removably receive the tight surface film (3) intended to form said at least one recess (35) for receiving said surgical materials and/or liquid products, wherein the tray (2) includes said means (5) for sticking said tight surface film (3) against said upper face (211) of the tray (2).

7. The equipment according to claim 1, wherein said tight surface film comprises an edge of the tight surface film comprising adhesive tapes suitable for maintaining its positioning on the tray before implementation of suction means.

* * * * *